United States Patent [19]
DeBoer et al.

[11] Patent Number: 5,717,106
[45] Date of Patent: Feb. 10, 1998

[54] CHROMENE DYES

[75] Inventors: Charles David DeBoer, Palmyra; Douglas Robert Robello; Lee William Tutt, both of Webster, all of N.Y.

[73] Assignee: Eastman Kodak Company, Rochester, N.Y.

[21] Appl. No.: 724,291

[22] Filed: Sep. 16, 1996

[51] Int. Cl.⁶ .................. C07D 311/58; C07D 405/06
[52] U.S. Cl. .................. 548/364.4; 544/300; 548/217; 549/372; 549/407
[58] Field of Search .................. 548/364.4; 549/407

[56] References Cited

U.S. PATENT DOCUMENTS 3,796,727  3/1974  DeBoer .

FOREIGN PATENT DOCUMENTS 591046  4/1994  European Pat. Off. .

OTHER PUBLICATIONS

D. Dauzonne, et al. in Eur. J. Med. Chem. 30(1), 53 (1995).

*Primary Examiner*—Robert W. Ramsuer
*Attorney, Agent, or Firm*—Harold E. Cole

[57] ABSTRACT

A yellow dye having the formula:

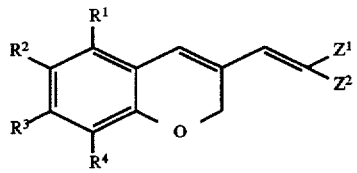

wherein:

$R^1$, $R^2$, $R^3$ and $R^4$ each independently represents hydrogen, halogen, or an alkoxy group of from 1 to about 6 carbon atoms; and $Z^1$ and $Z^2$ each independently represents cyano, esterified carboxy, amide, a substituted or unsubstituted benzoxazole, or alkylsulfonyl; or may be taken together to form a pyrazolone, barbituric acid or Meldrum's acid residue.

15 Claims, No Drawings

CHROMENE DYES

This invention relates to new chromene dyes which are of particular use in thermal imaging processes, such as thermal head dye transfer imaging or laser dye transfer or laser dye removal imaging.

Although many synthetic and natural dyes are known and have been used in many applications, not many dyes are useful in laser imaging processes because they do not meet all or many of the required criteria, such as cost, desired hue, resistance to light or chemical degradation, crystallinity requirements which may affect the power needed for effective printing speeds, etc. As will be shown hereafter, the dyes of the present invention exhibit properties which can be used to advantage in various imaging processes.

The following chromene compound:

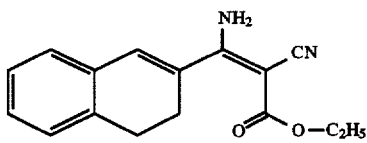

has been synthesized by S. M. Fahmy and R. M. Mohareb [Synthesis 6, 478 (1983)] and by H. Junck and F. Frosch [Z. Naturforsch. (B) 26, 1124 (1971)], wherein they showed two synthetic methods which produce this compound. However, this particular chromene is significantly different from the compounds of the present invention because of the amino functionality.

A number of naphthol chromenes, similar to the compounds of this invention have been disclosed by M. I. Sami, et at. [Tetrahedron 48, 5199 (1992)]. Other chromenes are disclosed by P. Bennett, et at. [J. Chem. Soc., Perkin Trans I (7) 688 (1973)]; EP 591,046; D. Dauzonne, et al. in Eur. J. Med. Chem. 30 (1), 53 (1995); and U.S. Pat. No. 3,796,727. However, these compounds all differ from the compounds of this invention.

The parent aldehyde used in preparing the compounds of this invention is disclosed by C. D. DeBoer [J. Org. Chem. 39 (16), 2426 (1974)]. However, this paper does not disclose the method for converting this aldehyde into the useful dyes of the present invention.

The dyes of the invention have the formula:

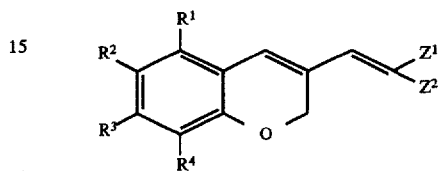

wherein:

$R^1$, $R^2$, $R^3$ and $R^4$ each independently represents hydrogen, halogen, or an alkoxy group of from 1 to about 6 carbon atoms; and $Z^1$ and $Z^2$ each independently represents cyano, esterified carboxy, amide, a substituted or unsubstituted benzoxazole, or alkylsulfonyl; or may be taken together to form a pyrazolone, barbituric acid or Meldrum's acid residue.

Examples of dyes included within the scope of the invention include the following:

| Dye | $R^1$ | $R^2$ | $R^3$ | $R^4$ | $Z^1$ | $Z^2$ |
|-----|-------|-------|-------|-------|-------|-------|
| 1 | H | H | H | H | CN | CN |
| 2 | H | H | H | H | CN | $COOC_2H_5$ |
| 3 | H | $OCH_3$ | H | H | CN | $COOC_2H_5$ |
| 4 | H | H | H | $OCH_3$ | CN | CN |
| 5 | H | H | H | H | | ![pyrazolone with N-phenyl, CH3] |
| 6 | H | Cl | H | H | CN | CN |
| 7 | H | Cl | H | H | CN | $COOC_2H_5$ |
| 8 | H | H | H | H | CN | $SO_2CH_3$ |
| 9 | H | H | H | H | CN | $COC_6H_5$ |
| 10 | H | H | H | H | | ![barbituric acid residue] |
| 11 | H | H | H | H | CN | ![5-chlorobenzoxazole] |
| 12 | H | H | H | H | | ![Meldrum's acid residue] |

-continued

| Dye | $R^1$ | $R^2$ | $R^3$ | $R^4$ | $Z^1$ | $Z^2$ |
|---|---|---|---|---|---|---|
| 13 | H | Br | H | H | CN | CN |
| 14 | H | H | H | H | $COOC_2H_5$ | $COOC_2H_5$ |
| 15 | Cl | H | H | H | $SO_2CH_3$ | $SO_2CH_3$ |
| 16 | $OCH_3$ | H | H | H | CN | $SO_2CH_3$ |
| 17 | $OCH_3$ | H | H | H | | |
| 18 | H | H | H | I | CN | |

Dyes 1–12 are shown as follows:

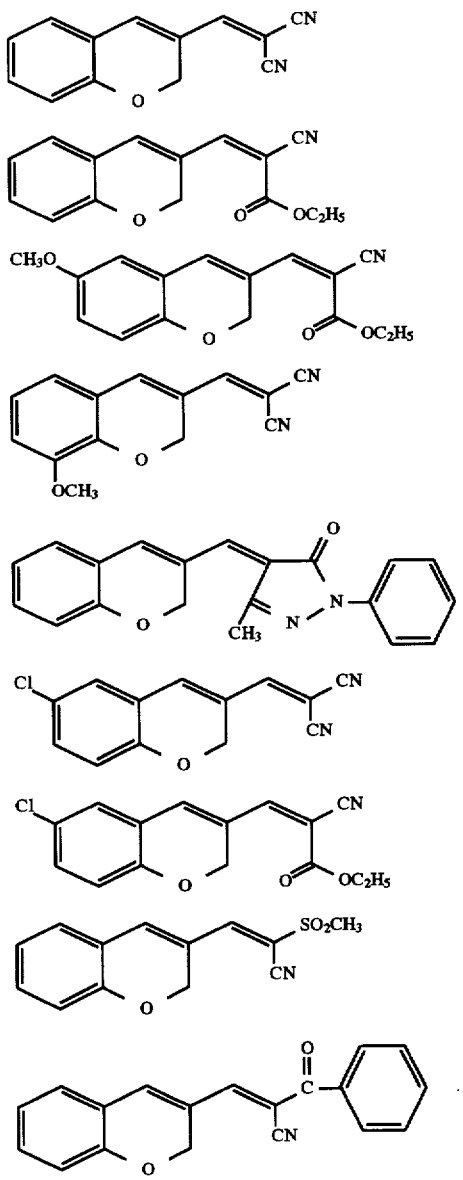

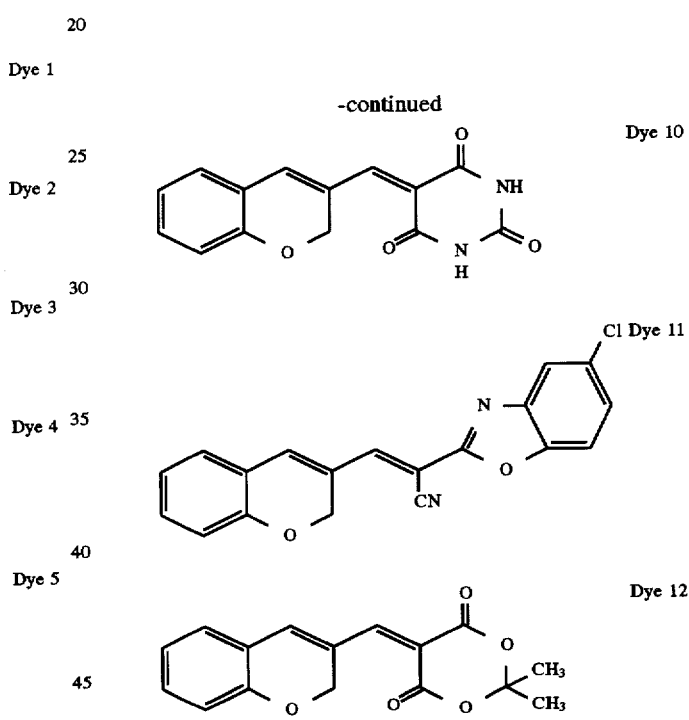

In a preferred embodiment of the invention, $R^1$, $R^3$ and $R^4$ each represent hydrogen and $R^2$ represents hydrogen or chloro. In another preferred embodiment, $Z^1$ represents CN and $Z^2$ represents CN, $COOC_2H_5$, $SO_2CH_3$ or $COC_6H_5$.

The above yellow dyes exhibit intense absorption in the blue region of the visible spectrum. Their relatively low molecular weights make them suitable for various imaging processes, such as thermal head and laser dye transfer printing processes and laser ablation or dye removal imaging processes. They have numerous hues which allows one to choose the most desired appearance. They can have significant absorption in the ultraviolet for masking properties. These dyes are also highly fluorescent but can be quenched by addition of mobile groups, as in the case with Dye 5, when this is undesirable. This class of dyes is simple to make and cheap to synthesize and are extremely versatile in usage.

The general approach to the synthesis of these dyes is shown below:

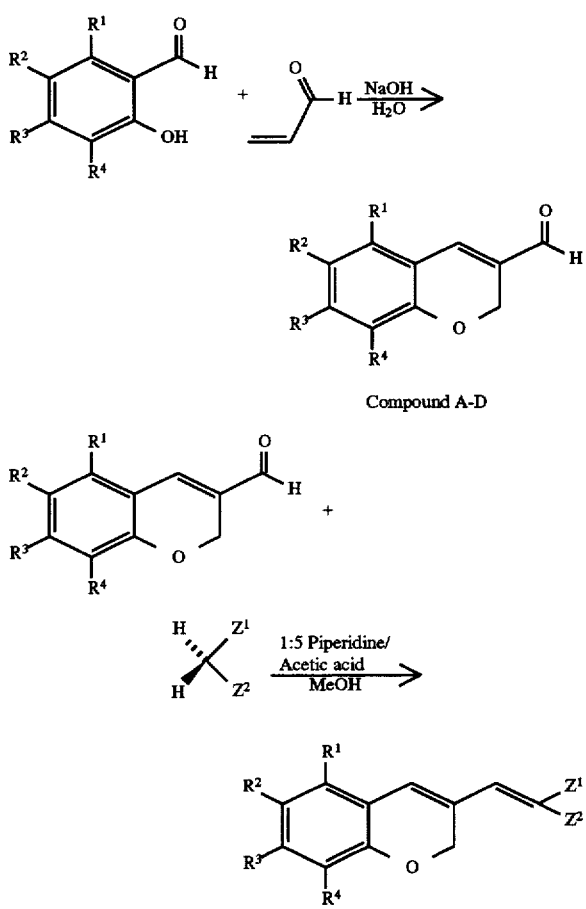

Compound A-D

The following examples are provided to illustrate the invention.

EXAMPLE 1

Chromene 3-carboxaldehyde (Compound A)

One mole of salicaldehyde was stirred with 3 liter of $H_2O$ and 0.05 mole NaOH. A stream of nitrogen was bubbled through 1.5 mole acrolein and then into the salicaldehyde-water mixture. When all the acrolein had been driven into the solution (16 hours), the mixture was acidified with 0.06 mole HCl, extracted with methylene chloride and the product separated by vacuum distillation as a pale yellow solid.

EXAMPLE 2

8-Methoxy-chromene 3-carboxaldehyde (Compound B)

One mole of o-vanillin was stirred with 3 liter $H_2O$ and 0.05 mole NaOH. A stream of nitrogen was bubbled through 1.5 moles acrolein and then into the o-vanillin-water mixture. When all the acrolein had been driven into the solution (16 hours) the mixture was acidified with 0.06 mole of HCl and the intermediate product (a light yellow crystalline solid) was filtered off and washed with $H_2O$.

EXAMPLE 3

6-Methoxy-chromene 3-carboxaldehyde (Compound C)

5-Methoxy salicaldehyde (4.0 g) was added to 100 ml $H_2O$. To the mixture was added 0.25 g NaOH, followed by dropwise addition of 4.0 g acrolein, and the solution was stirred for 24 hrs. Afterwards the solution was slightly acidified with HCl and the precipitate filtered off and washed with $H_2O$.

EXAMPLE 4

6-Chloro-chromene 3-carboxaldehyde (Compound D)

The procedure from Synthetic Example 3 was followed starting from 2-hydroxy-5-chlorobenzaldehyde (4.0 g).

EXAMPLE 5

Dye 1

The product of Synthetic Example 1 (Compound A) was dissolved in 1 liter methanol along with 50 grams of malononitrile. Then 200 mg of a 5:1 mixture of acetic acid and piperidine was added. After standing for another hour, the yellow brown crystals were filtered off, washed with water and recrystallized from hot methanol. NMR analysis proved to be consistent with the structure as shown.

Calculated 75.0% C 3.9% H 13.5% N

Experimental 74.2% C 4.0% H 13.0% N

EXAMPLE 6

Dye 2

The product of Synthetic Example 1 (Compound A, approx. 4 g) was placed in 30 g of methanol, brought to a boil, and 1.0 gm of ethyl cyanoacetate was added along with a couple of drops of a 5:1 mixture of acetic acid and piperidine. The solution was boiled for 15 min. and the precipitate removed and recrystallized from methanol. The product was isolated as light yellow crystals.

Calculated 70.6% C 5.1% H 5.5% N

Experimental 70.1% C 5.1% H 5.6% N

EXAMPLE 7

Dye 3

The procedure from Example 6 was followed starting from the product of Synthetic Example 3 (Compound C) and ethyl cyanoacetate.

Calculated 67.4% C 5.3% H 4.9% N

Experimental 67.5% C 5.3% H 5.1% N

EXAMPLE 8

Dye 4

The product of Synthetic Example 2 (Compound B) was dissolved in 1 liter methanol with 50 g malononitrile. Then 200 mg of a 5:1 mixture of acetic acid and piperidine was added. After standing for another hour, the yellow crystals were filtered off and washed with water. NMR analysis proved to be consistent with the structure shown for Dye 4.

Calculated 70.6% C 4.2% H 11.8% N

Experimental 70.5% C 4.3% H 11.5% N

EXAMPLE 9

Dye 5

The procedure from Example 6 was followed starting from the product of Synthetic Example 2 (Compound B) and 3-methyl-1-phenyl-2-pyrazolin-5-one. After the reaction, the methanol was removed and the oil was extracted with methylene chloride and the solution filtered through silica gel. The methylene chloride was removed and the product recrystallized from acetone. The product was isolated as dark reddish crystals.

Calculated 75.9% C 5.1% H 8.9% N

Experimental 75.6% C 5.2% H 8.7% N

Mass spectrum parent peak 316 amu, theoretical 316.

EXAMPLE 10

Dye 6

The procedure from Example 6 was followed starting from the product of Synthetic Example 4 (Compound D) and malononitrile. The product was isolated as a yellow powder.

Calculated 64.3% C 2.9% H 10.8% N

Experimental 64.1% C 3.1% H 11.5 % N

EXAMPLE 11

Dye 7

The procedure from Example 6 was followed starting from the product of Synthetic Example 2 (Compound D) and ethyl cyanoacetate. The product was isolated as an orange powder.

Calculated 62.2% C 4.2% H 4.8% N

Experimental 60.9% C 4.1% H 5.1% N

EXAMPLE 12

Dye 8

A stirred solution of 4.00 g (25 mmol) of the product from Synthetic Example 1 (Compound A), 3.27 g (27 mmol) methyl sulfonyl acetonitrile, 4 drops of piperidine, and 50 ml ethanol was heated at reflux for 16 hrs, and then cooled to −10° C. The resulting yellow precipitate was collected and washed with cold methanol, and then air-dried. The product was recrystallized from acetonitrile and then dried in vacuo over $CaSO_4$ to provide 3.8 g (58%) yellow crystals.

Calculated 59.76% C 4.24% H 5.36% N 12.27% S

Experimental 59.74% C 4.07% H 5.32% N 11.83% S

EXAMPLE 13

Dye 9

A stirred solution of 5.00 g (31 mmol) the product from Synthetic Example 1 (Compound A), 4.98 g (34 mmol) benzoylacetonitrile, 4 drops piperidine, and 50 ml ethanol was heated at reflux for 2 hrs, and then cooled to 25° C. The resulting orange precipitate was collected and washed with cold methanol, and then air-dried. The product was recrystallized from toluene, and then dried in vacuo over $CaSO_4$ to provide 4.1 g (46%) orange crystals.

Calculated 79.43% C 4.56% H 4.87% N

Experimental 79.90% C 4.78% H 4.74% N

EXAMPLE 14

Dye 10

A stirred suspension of 5.00 g (31 mmol) the product from Synthetic Example 1 (Compound A), 4.40 g (34 mmol) of barbituric acid, 4 drops piperidine, and 25 ml ethanol was heated at reflux for 4 hrs, and then cooled to 25° C. The resulting orange precipitate was collected and washed with cold methanol, and then air-dried. The product was recrystallized from pyridine, and then dried in vacuo at 80° C. to provide 4.5 g (53%) orange crystals.

Calculated 62.22% C 3.73% H 10.37% N

Experimental 62.34% C 4.02% H 10.44% N

EXAMPLE 15

Dye 11

A stirred suspension of 5.00 g (31 mmol) the product from Synthetic Example 1 (Compound A), 6.61 g (34 mmol) 5-chloro-2-benzoxazolacetonitrile, 4 drops piperidine, and 50 ml ethanol was heated at reflux for 5 hrs, and then cooled to 25° C. The resulting orange precipitate was collected and washed with cold methanol, and then air-dried. The product was recrystallized from pyridine, and then dried in vacuo at 80° C. to provide 7.1 g (68%) orange crystals.

Calculated 68.17% C 3.31% H 8.37% N 10.59% Cl

Experimental 68.27% C 3.74% H 8.44% N 10.16% Cl

EXAMPLE 16

Dye 12

A stirred mixture of 5.00 g (31 mmol) the product from Synthetic Example 1 (Compound A), 4.95 g (34 mmol) 2-2-dimethyl-1,3-dioxane-4,6-dione (Meldrum's acid), 0.5 ml acetic acid, 4 drops of piperidine, and 40 ml of toluene was heated at reflux for 18 hrs with continuous azeotropic removal of water. The reaction mixture was cooled to 25° C., and then the resulting orange precipitate was collected, washed with cold methanol, and air-dried. The product was recrystallized from toluene, and then dried in vacuo over $CaSO_4$ to provide 1.0 g (11%) orange crystals.

Calculated 67.13% C 4.93% H

Experimental 67.32% C 4.97% H

EXAMPLE 17

The dyes of the present invention were compared against the following control dyes:

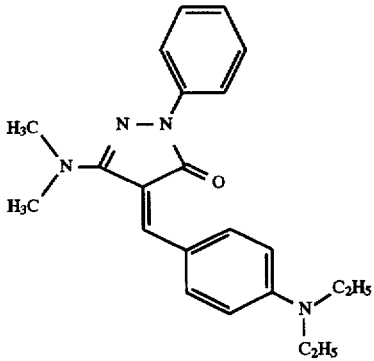

Control 1
(Thermal dye transfer yellow dye as shown in U.S. Patent 4,866,029)

-continued

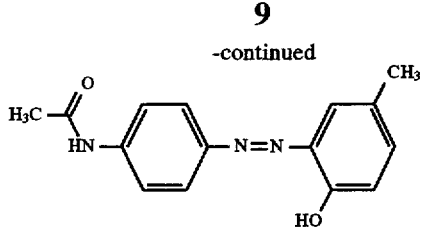

Keyplast Yellow GC-Control 2
(Laser Dye Ablation yellow dye as shown in U.S. Patent 5,521,050)

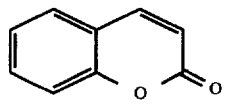

Coumarin-Control 3
(U.S. Patent 4,876,237)
Structurally similar dye

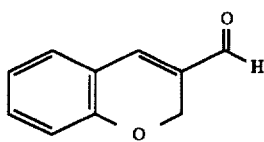

Chromene carboxaldehyde-Control 4
(U.S. Patent 3,796,727)
Structurally similar dye Spectral data were obtained for the dyes listed below in Table 1 in methyl isobutyl ketone (except for Dye 10, which was measured in dimethyl sulfoxide) using approximately 5 mg of dye in 100 ml of solvent in a 1 cm cell.

TABLE 1

| Dye | Wavelength $\lambda_{max}$(nm) | Extinction Coefficient* $\epsilon$ (L/mol/cm) |
| --- | --- | --- |
| Control 1 | 446 | 45,700 |
| Control 2 | 358 | 20,400 |
| Control 3 | <320 | NM |
| Control 4 | 355 | 6,400 |
| 1 | 414 | 17,050 |
| 2 | 405 | 15,050 |
| 3 | 435 | 11,700 |
| 4 | 425 shoulder | 9,900 |
| 5 | 410 | 13,700 |
| 6 | 415 | 13,200 |
| 7 | 405 | 14,000 |
| 8 | 405 | 13,900 |
| 9 | 404 | 13,100 |
| 10 | 422 | 16,500 |
| 11 | 421 | 24,600 |
| 12 | 417 | 14,100 |

*Liters per mole per cm
NM = Not measured

DYE-DONOR ELEMENT

Dye-donor elements were prepared by applying a slipping layer on the backside of a 12.5 μm poly(ethylene terephthalate) film consisting of a coating mixture of 0.38 g/m² poly(vinyl acetal) (KS-1 from Sekisui Corp.), 0.02 g/m² candelilla wax, 0.003 g/m² p-toluenesulfonic acid, and 0.01 g/m² (PS-513 from Huels America) coated from diethyl ketone. The dye coating was then applied to the front side of the support consisting of 0.27 g/m² of the respective dye and 0.32 g/m² cellulose acetate propionate (20 sec viscosity).

PRINTING

A dye-receiving element was prepared by coating a mixture of Makrolon 5705® (Bayer AG Corporation) polycarbonate resin (2.9 g/m²) and Tone-PCL300® polycaprolactone (Union Carbide Co.) (0.8 g/m²) in dichloromethane on a titanium dioxide pigmented polyethylene-overcoated paper stock.

The dye side of the dye-donor element of 10 cm×15 cm in area, was placed in contact with the dye image-receiving layer side of the dye-receiving element of the same area. This assemblage was clamped to a stepper motor-driven, 60 mm diameter rubber roller. A thermal head (TDK No. 8I0630, thermostatted at 31° C.) was pressed with a force of 24.4 Newton (2.5 kg) against the dye-donor element side of the assemblage, pushing it against the rubber roller.

The imaging electronics were activated, causing the donor-receiver assemblage to be drawn through the printing head/roller nip at 11.1 mm/s. Coincidentally, the resistive elements in the thermal print head were pulsed (128 ms/pulse) at 129 ms intervals during a 16.9 ms/dot printing cycle. A stepped image density was generated by incrementally increasing the number of pulses/dot from a minimum of 0 to a maximum of 127 pulses/dot. The voltage supplied to the thermal head was approximately 13.00 v resulting in an instantaneous peak power of 0.214 watts/dot and a maximum total energy of 3.48 mj/dot.

After printing, the dye-donor element was separated from the imaged receiving element and the a*b*L* parameters measured of the maximum coloration patch (the 127 pulses/dot) using an X-Rite spectrodensitometer (Model 938) from X-rite Inc., Grandville, Mich. as follows.

TABLE 2

| Dye | a* | b* | L* |
| --- | --- | --- | --- |
| Blank receiver | −0.08 | −2.95 | 91.8 |
| Control 1 | 4.01 | 105 | 77.3 |
| Control 2 | −17.9 | 77.4 | 87.2 |
| Control 3 | −0.33 | −3.13 | 90.9 |
| Control 4 | −.30 | −3.03 | 91.2 |
| 1 | −9.78 | 40.9 | 90.2 |
| 2 | −15.4 | 53.1 | 90.8 |
| 3 | 4.66 | 86.7 | 88.0 |
| 4 | −6.88 | 74.0 | 88.0 |
| 5 | 10.3 | 66.6 | 76.4 |
| 8 | −23.1 | 57.5 | 90.7 |
| 9 | −17.7 | 76.5 | 88.2 |
| 10 | −2.88 | 35.5 | 87.2 |
| 11 | −4.30 | 19.2 | 89.9 |
| 12 | −13.4 | 92.8 | 85.7 |

Since hue is related to a* and b* values, a higher b* value indicates a purer yellow hue. It can be seen from the b* values that all dyes are better yellow dyes than are Control 3 and Control 4.

The receivers containing the transferred dye images were placed under a near UV lamp and the color of any fluorescence noted. The wavelength maxima were found by using a Perkin Elmer Fluorescence Spectrophotometer, (Model LS-5), to excite the dye on the prior samples at 360 nm and then scanning the resulting fluorescence. The following results were obtained:

TABLE 3

| Dye | Color | Peak Wavelengths (nm) |
| --- | --- | --- |
| Blank receiver | light white | 434,491 |
| Control 1 | very dim light yellow brown | ND* |
| Control 2 | ND | ND |
| Control 3 | ND | ND |

TABLE 3-continued

| Dye | Color | Peak Wavelengths (nm) |
|---|---|---|
| Control 4 | ND | ND |
| 1 | lemon yellow | 543 |
| 2 | greenish-yellow | 527 |
| 3 | bright orange | 588 |
| 4 | bright orange-yellow | 569 |
| 5 | ND | ND |
| 8 | bright yellow | 537 |
| 9 | orange | 565 |
| 10 | dim red | 587 |
| 11 | orange | 554 (broad) |
| 12 | orange | 580 |

*ND - None Detected

The above data shows that most of the chromene dyes possess strong fluorescence with the exception of Dye 5. Although Dye 10 is dim, it has a red fluorescence which is different and could be used when so desired.

EXAMPLE 18

To a 100 μm thick poly(ethylene terephthalate) support was applied a coating of each of the above dyes consisting of 0.54 g/m² nitrocellulose, 0.27 g/m² dye and 0.16 g/m² infrared dye IR-1 from a methyl isobutyl ketone/ethanol (3:1) solvent mixture.

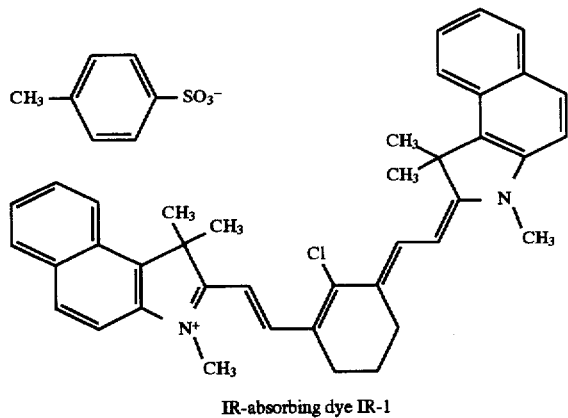

IR-absorbing dye IR-1

Each of the coatings was ablation written using a laser diode print head, where each laser beam has a wavelength range of 830–840 nm and a nominal power output of 600 mW at the film plane. The drum, 53 cm in circumference was rotated at varying speeds and the imaging electronics were activated to provide adequate exposure. The translation stage was incrementally advanced across the dye ablation element by means of a lead screw turned by a microstepping motor, to give a center-to-center line distance of 10.58 μm (945 lines per centimeter or 2400 lines per inch). An air stream was blown over the dye ablation element surface to remove the ablated dye. The ablated dye and other effluents are collected by suction. The measured total power at the focal plane was 600 mW per channel. At a rotation of 1040 rpm, the exposure was about 620 mj/cm². The Status A Blue optical density of the imaged area and the non-imaged areas were measured using an X-Rite Photographic Densitometer (Model 310). The following results were obtained:

TABLE 4

| Dye | Status A Yellow Dmin | Status A Yellow Dmax |
|---|---|---|
| Control 1 | 0.14 | 3.20 |
| Control 2 | 0.08 | 1.14 |
| Control 3 | 0.06 | 0.18 |
| Control 4 | 0.07 | 0.24 |
| 1 | 0.16 | 0.95 |
| 2 | 0.10 | 1.14 |
| 3 | 0.10 | 1.41 |
| 4 | 0.10 | 1.38 |
| 5 | 0.09 | 1.13 |
| 8 | 0.09 | 0.99 |
| 9 | 0.11 | 1.38 |
| 10 | 0.12 | 1.75 |
| 12 | 0.10 | 1.61 |

The above data show that most of the dye was removed in the non-imaged or Dmin areas and that a useful image was achieved. The lower Dmax reflects the different hues and the different extinction coefficients of the various dyes. Higher Dmax could be achieved by higher laydowns. Because of their higher Dmax values, the chromenes are better yellow dyes than are Control 3 and Control 4 for laser dye ablation.

EXAMPLE 19

Coatings of each of the dyes were made as in Example 2. To the printing drum of Example 2 was placed a sheet of Kodak Approval® Intermediate Receiver as disclosed in U.S. Pat. No. 5,300,398. The coatings were placed dye side down against the Intermediate receiver. The material was printed as in Example 2 except that exposure occurred through the coating support. The coating and receiver were separated and the receiver was laminated to paper at a temperature of 125° C. using a Kodak Approval® Laminator. The Status A blue density of the transferred dye was then measured using an X-Rite Photographic Densitometer (Model 310) fitted with a reflection head. The following results were obtained:

TABLE 5

| Dye | Status A Blue |
|---|---|
| Control 1 | 1.88 |
| Control 2 | 1.29 |
| Control 3 | 1.69 |
| Control 4 | 0.55 |
| 1 | 0.88 |
| 2 | 0.67 |
| 3 | 0.96 |
| 4 | 0.96 |
| 5 | 0.73 |
| 8 | 1.21 |
| 9 | 1.28 |
| 10 | 1.42 |
| 12 | 1.41 |

It is apparent that the dyes transferred well. The different densities reflect the different hues and extinction coefficients. Larger densities can be obtained by using a higher laydown in the donor coating. All the chromene dyes transferred better than did Control 3 and Control 4.

The invention has been described in detail with particular reference to preferred embodiments thereof, but it will be understood that variations and modifications can be effected within the spirit and scope of the invention.

What is claimed is:

1. A yellow dye having the formula:

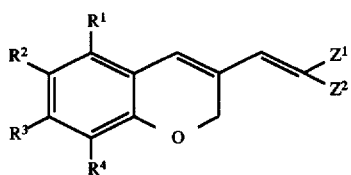

wherein:

$R^1$, $R^2$, $R^3$ and $R^4$ each independently represents hydrogen, halogen, or an alkoxy group of from 1 to about 6 carbon atoms; and $Z^1$ and $Z^2$ each independently represents cyano, esterified carboxy, amide, a substituted or unsubstituted benzoxazole, or alkylsulfonyl; or may be taken together to form a pyrazolone, barbituric acid or Meldrum's acid residue.

2. The dye of claim 1 wherein $R^1$, $R^3$ and $R^4$ each represent hydrogen and $R^2$ represents hydrogen or chloro.

3. The dye of claim 1 wherein $Z^1$ represents CN and $Z^2$ represents CN, $COOC_2H_5$, $SO_2CH_3$ or $COC_6H_5$.

4. The dye of claim 1 which has the following formula:

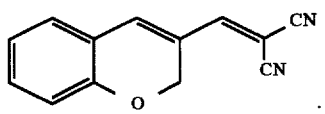

5. The dye of claim 1 which has the following formula:

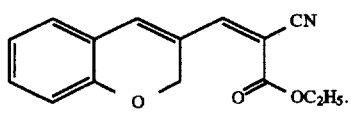

6. The dye of claim 1 which has the following formula:

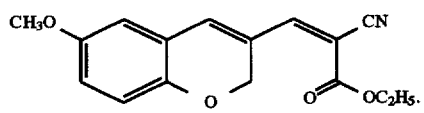

7. The dye of claim 1 which has the following formula:

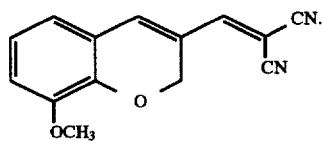

8. The dye of claim 1 which has the following formula:

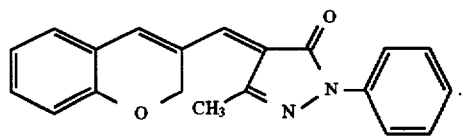

9. The dye of claim 1 which has the following formula:

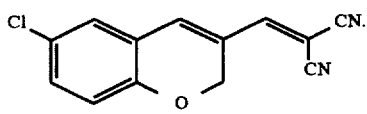

10. The dye of claim 1 which has the following formula:

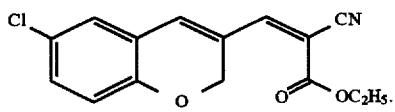

11. The dye of claim 1 which has the following formula:

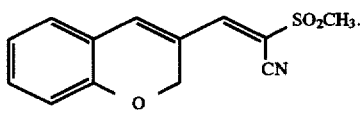

12. The dye of claim 1 which has the following formula:

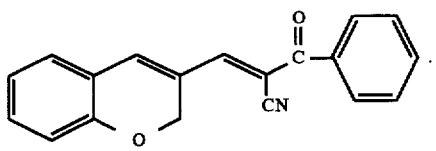

13. The dye of claim 1 which has the following formula:

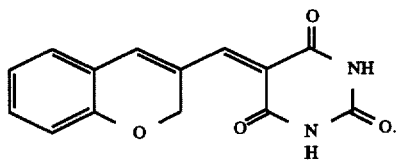

14. The dye of claim 1 which has the following formula:

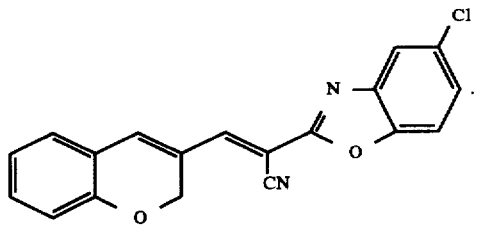

15. The dye of claim 1 which has the following formula:

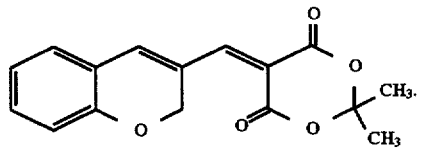

* * * * *